United States Patent
Briggs et al.

(10) Patent No.: US 11,132,712 B2
(45) Date of Patent: Sep. 28, 2021

(54) METHOD FOR USING 3D POSITIONAL SPATIAL OLFACTION FOR VIRTUAL MARKETING

(71) Applicant: INTERNATIONAL BUSINESS MACHINES CORPORATION, Armonk, NY (US)

(72) Inventors: Benjamin D. Briggs, Waterford, NY (US); Lawrence A. Clevenger, Rhinebeck, NY (US); Leigh Anne H. Clevenger, Rhinebeck, NY (US); Christoper J. Penny, Saratoga Springs, NY (US); Michael Rizzolo, Albany, NY (US); Aldis Sipolins, New York City, NY (US)

(73) Assignee: International Business Machines Corporation, Armonk, NY (US)

( * ) Notice: Subject to any disclaimer, the term of this patent is extended or adjusted under 35 U.S.C. 154(b) by 565 days.

(21) Appl. No.: 15/783,028

(22) Filed: Oct. 13, 2017

(65) Prior Publication Data
US 2019/0114671 A1    Apr. 18, 2019

(51) Int. Cl.
*G06Q 30/00* (2012.01)
*G06Q 30/02* (2012.01)
(Continued)

(52) U.S. Cl.
CPC ............ *G06Q 30/0261* (2013.01); *A61L 9/00* (2013.01); *G06F 3/04815* (2013.01); *A61L 9/03* (2013.01);
(Continued)

(58) Field of Classification Search
None
See application file for complete search history.

(56) References Cited

U.S. PATENT DOCUMENTS

| 7,484,716 B2 | 2/2009 | Morie et al. |
| 2013/0024756 A1* | 1/2013 | Basso ................... G06F 3/165 715/202 |

(Continued)

FOREIGN PATENT DOCUMENTS

| CN | 204666957 U | 9/2015 |
| EP | 0665039 A1 | 8/1995 |

(Continued)

OTHER PUBLICATIONS

Madrigal, Alexis, Researchers Want to Add Touch, Taste and Smell to Virtual Reality, Mar. 4, 2009, wired.com, 4 pp (Year: 2009).*

(Continued)

*Primary Examiner* — Michael W Schmucker
(74) *Attorney, Agent, or Firm* — Teddi E. Maranzano (57) ABSTRACT

Three-dimensional positional spatial olfaction for virtual marketing associates a product with a product location within a virtual reality environment and identifies a product aroma associated with the product. A distance and a direction from the product location to a positional presence of a participant within the virtual reality environment is determined, and the product aroma is delivered to the participant in accordance with the distance and the direction. Delivery of the product aroma to the participant in accordance with the distance and the direction is used to lead the participant through the virtual reality environment to the product location where an interface for obtaining a physical copy of the product is displayed to the participant.

17 Claims, 7 Drawing Sheets

(51) Int. Cl.
*A61L 9/00* (2006.01)
*G06F 3/0481* (2013.01)
*A61L 9/14* (2006.01)
*A61L 9/03* (2006.01)
*A61L 9/12* (2006.01)

(52) U.S. Cl.
CPC . *A61L 9/12* (2013.01); *A61L 9/14* (2013.01); *A61L 2209/111* (2013.01); *A61L 2209/133* (2013.01)

(56) References Cited

U.S. PATENT DOCUMENTS

| | | | |
|---|---|---|---|
| 2018/0071425 A1* | 3/2018 | Jin | A61L 9/14 |
| 2018/0286351 A1* | 10/2018 | Fateh | G09G 5/12 |
| 2019/0043264 A1* | 2/2019 | Tomizuka | H04L 67/38 |

FOREIGN PATENT DOCUMENTS

| | | | | |
|---|---|---|---|---|
| JP | 4677633 B2 | | 4/2011 | |
| WO | 2008081413 A1 | | 7/2008 | |
| WO | WO 2010/124074 | * | 10/2010 | G06F 3/048 |
| WO | 2016164917 A1 | | 10/2016 | |

OTHER PUBLICATIONS

May, Gareth, Fifth Sense: The next stage of VR is total sensory immersion, May 17, 2017, wareable.com, 8pp (Year: 2017).*

Bolton, Adam, VR smells aren't just for porn, they're coming to games too, Jan. 20, 2017, cnet.com, 9pp (Year: 2017).*

American Industrial Hygiene Association (AIHA), "Odor Thresholds for Chemicals with Established Health Standards, 2nd Edition," published Apr. 23, 2013, pp. 21-182, retrieved from www.knovel.com, http://www.pdo.co.om/hseforcontractors/Health/Documents/HRAs/ODOR%20THRESHOLDS.pdf.

Cakebread, "Virtual reality gets smelly thanks to this Japanese startup," Business Insider, Jun. 27, 2017, http://www.businessinsider.com/japanese-startup-vaqso-adding-smells-virtual-reality-2017-6.

Feelreal, "VR Mask," http://feelreal.com, retrieved Oct. 12, 2017.

Monks, "Forget text messaging, the 'oPhone' lets you send smells," CNN, Mar. 17, 2014, http://www.cnn.com/2014/03/17/tech/innovation/the-ophone-phone-lets-you-send-smells/index.html.

Twilley, "Will Smell Ever Come to Smartphones?" The New Yorker, Apr. 27, 2016, https://newyorker.com/tech/elements/is-digital-smell-doomed.

Wikipedia, "Aroma compound," retrieved Oct. 12, 2017, https://en.wikipedia.org/wiki/Aroma_compound.

Aiken, et al., "Posttraumatic stress disorder: possibilities for olfaction and virtual reality exposure therapy," Virtual Reality, 2015, pp. 95-109, vol. 19, DOI: 10.1007/s10055-015-0260-x, Retrieved from the Internet: <URL: https://link.springer.com/article/10.1007/s10055-015-0260-x>.

Catania, "Stereo and serial sniffing guide navigation to an odour source in a mammal," Nature Communications, Feb. 5, 2013, vol. 4, Art. 1441, DOI: 10/1038/ncomms2444, Retrieved from the Internet: <URL: https://www.nature.com/articles/ncomms2444>.

Feelreal, Datasheet [online], FeelReal, Inc., [accessed on Feb. 18, 2021 ], Retrieved from the Internet: <URL: https://feelreal.com/>.

Munyan III, et al., "Olfactory Stimuli Increase Presence in Virtual Environments," PLOS ONE Research Article, Jun. 16, 2016, 19 pages, DOI:10.1371/journal.pone.0157568, Retrieved from the Internet: <URL: https://journals.plos.org/plosone/article?id=10.1371/journal.pone.0157568>.

* cited by examiner

METHOD FOR USING 3D POSITIONAL SPATIAL OLFACTION FOR VIRTUAL MARKETING

FIELD OF THE INVENTION

The present invention relates to virtual reality and olfaction in virtual reality environments.

BACKGROUND OF THE INVENTION

Currently, marketing in virtual environments is limited to visual and auditory modalities. For example, companies place virtual billboards in virtual environments to catch the attention of users. However, such billboards are easily ignored, and products without strong visual identities are ill suited to visual ads.

Smell generators have been integrated into virtual reality displays. Conventional smell generators are either on or off. Since smells have been shown to increase the feeling of "presence" in virtual reality, olfaction is a potentially useful tool for enhancing immersion. In addition, animals, including humans, can localize smells based on the relative strength of the smell in each nostril through a mechanism that is similar though less precise to the localization of sounds. Therefore, systems and methods are desired that can improve the marketing of products in virtual realities using the enhanced immersion and localization qualities of smells introduced into virtual reality.

SUMMARY OF THE INVENTION

Exemplary embodiments are directed to systems and methods for product placement in a virtual reality environment using olfactory technology. Effectiveness of product placement in the virtual reality environment is enhanced using advances in olfactory technology. In one embodiment, virtual reality headsets with integrated smell generators in the head-mounted displays (HMDs) are used. These virtual reality headsets allow base smells to be combined into appealing smells ranging, for example, from cinnamon buns to french fries. These appealing smells can be associated with a product or with an environment, e.g., store or restaurant, where the product is sold. In addition, the appealing smells can be generic smells or smells that are proprietary to a given product or environment.

The products are associated with one or more specific product locations within the virtual reality environment. For example, a given product or given set of products is associated with a store front or restaurant occupying a unique space, set of coordinates or position within the virtual reality environment. In one embodiment, each product location is established by a producer or seller of a given product by purchasing one or more specific product locations, i.e., sets of coordinates, within the virtual reality environment to be associated with the given product. One or more occupants or participants in the virtual reality environment also have an associated presence, position or set of coordinates within the virtual reality environment at any given point in time. Therefore, a spatial relationship exists within the virtual reality environment between any given product location and any given occupant or participant. This spatial relationship includes distance and direction, e.g., is a vector quantity. As occupants or participants move within the virtual reality environment, the spatial relationships, i.e., distance and direction, between a given occupant and a given product location change over time. The smell-enabled virtual reality headsets provide scents or aromas to a given occupant or participant in accordance with a current spatial relationship. For example, the smell-enabled virtual reality headsets indicate distance by varying the overall intensity of a given product aroma. Direction is indicated by varying product aroma intensity separately in each nostril, allowing occupants or participants to localize these aromas in 3D space based on the difference in aroma intensity between both nostrils.

The ability to vary intensity is used to direct an occupant or participant toward the product location. For example, both nostrils receive equal amounts of the aromas as a participant turns their head toward the product location, informing the participant that the product location is now directly in front of the participant. As the participant, or the avatar associated with the participant, approaches the product location within the virtual reality environment, the overall intensity of the product aroma increases, informing the participant that they are approaching the product location of the product associated with that aroma. Upon approaching the product location, the participant is provided with a visual display of the product and an interface for purchasing the product within the virtual reality environment. Once purchased, the purchased products can be physically delivered, for example, using drones or a delivery service, to the participant at the actual physical location of the participant. Upon at least one of ordering the product, receiving delivery of the product or use or consumption of the product, the aromas of the product can be delivered to other active occupants or participants in the virtual reality environment based, for example, on a spatial relationship between any other participant and the participant ordering, receiving, consuming or using the product.

The other participants can be directed to the participant ordering, receiving, consuming or using the product, and once in proximity to the participant ordering, receiving, consuming or using the product are provided with the ability to order the same or similar products. The generation of aromas associated with the participant ordering, receiving, consuming or using the product can be terminated based on time, complete consumption of the product or stopping use of the product. Olfactory advertising in virtual reality environments is more interactive and provides increased engagement between the participants and products over conventional advertising methods such as commercials. In addition, olfactory advertising is less obtrusive and allows simultaneous competition among multiple vendors in a single virtual reality environment.

Exemplary embodiments are directed to a method for using three-dimensional positional spatial olfaction for virtual marketing by associating a product with a product location within a virtual reality environment, identifying a product aroma associated with the product, determining a distance and a direction from the product location to a positional presence of a participant within the virtual reality environment, delivering the product aroma to the participant in accordance with the distance and the direction, using delivery of the product aroma to the participant in accordance with the distance and the direction to lead the participant through the virtual reality environment to the product location and displaying an interface for obtaining a physical copy of the product to the participant within the virtual reality environment at the product location.

Exemplary embodiments are directed to a method for using three-dimensional positional spatial olfaction for virtual marketing by associating each one of a plurality of products with a unique product location within a virtual reality environment, identifying a product aroma associated with each product, determining a distance and a direction from each product location to a positional presence of a participant within the virtual reality environment, delivering each product aroma to the participant in accordance with the distance and the direction, using delivery of each product aroma to the participant in accordance with the distance and the direction to lead the participant through the virtual reality environment to at least one of the product locations and displaying an interface for obtaining a physical copy of a given product to the participant within the virtual reality environment at the product location associated with the given product.

Exemplary embodiments are directed to a system for using three-dimensional positional spatial olfaction for virtual marketing. The system includes a computing system running an instance of a virtual reality environment and an interface device in communication with the computing system and associated with a participant. The interface device provides a display of the virtual reality environment to the participant at a positional presence within the virtual reality environment. A product location module executes on the computing system to associate a product location within the virtual reality environment with a product, and an aroma determination mechanism executes on the computing system to determine an aroma associated with the product. Aa spatial determination mechanism executes on the computing system to determine a distance and a direction from the product location to the positional presence of the participant, and an aroma delivery mechanism associated with the interface device and in communication with the aroma determination mechanism and the spatial determination mechanism delivers the product aroma to the participant in accordance with the distance and the direction to lead the participant through the virtual reality environment to the product location. A product acquisition module executes on the computing system to display to the participant an interface for obtaining a physical copy of the product within the virtual reality environment at the product location.

DETAILED DESCRIPTION

Figure 1:
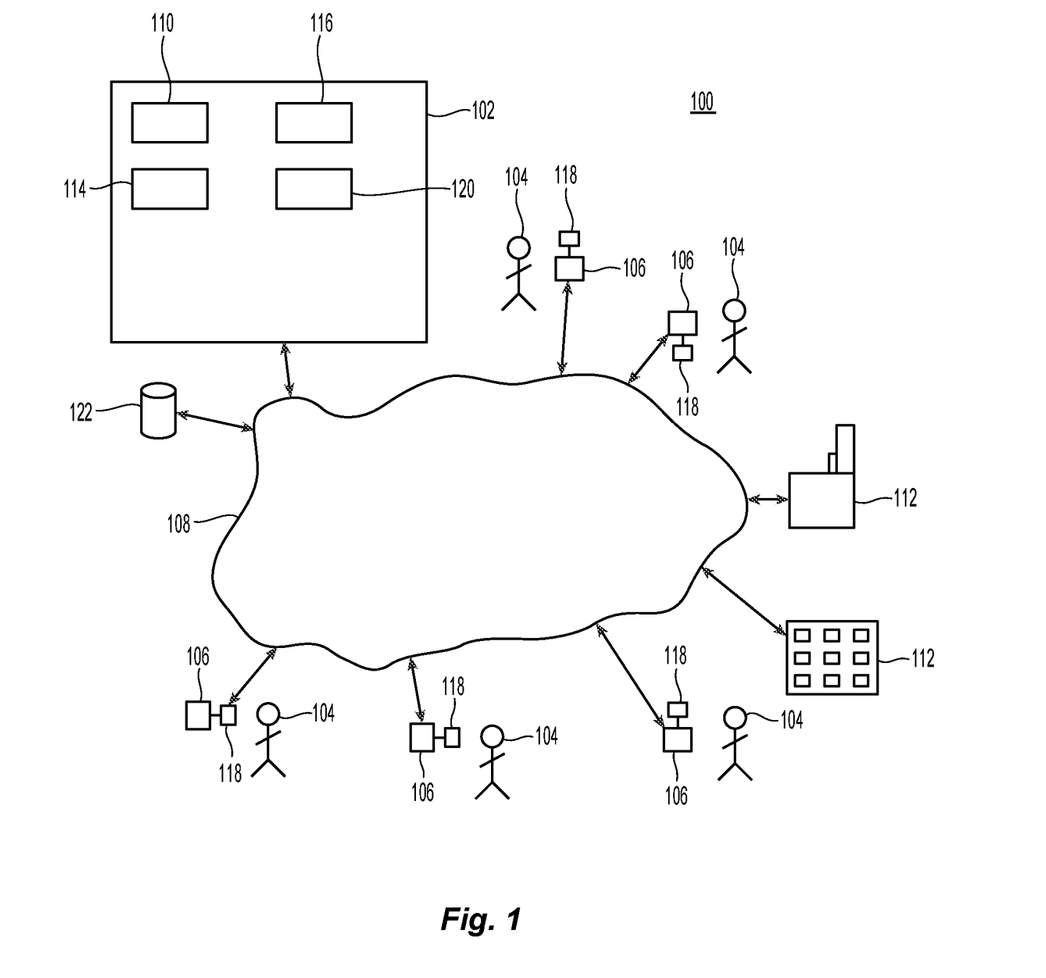
FIG. 1 is a schematic representation of an embodiment of a system for using three-dimensional positional spatial olfaction for virtual marketing.

Referring initially to FIG. 1, exemplary embodiments are directed to a system for using three-dimensional (3D) positional spatial olfaction for virtual marketing 100. The system includes at least one computing system 102. Suitable computing systems include, but are not limited to, stand along computers and servers and distributed networks of computers and servers running a distributed computing system. The computing system is running an instance of a virtual reality environment. Any suitable virtual reality environment known and available in the art including gaming environments in which one or more participants 104 navigate through and interact with each other and with the virtual reality environment can be used.

At least one interface device 106 is provided in communication with the computing system across one or more local or wide area networks 108. When a plurality of participants is using the virtual reality environment, the system includes a plurality of interface devices. Each interface device is associated with one a given participant. The interface device provides a display of the virtual reality environment to the participant. Suitable interface devices include one or more computer monitors or similar displays, including touch screens, and head-mounted displays (HMDs). The interface devices can also include haptic devices, devices to provide sound and devices to provide scents or aromas. In one embodiment, the HMD is worn by the participant and provides visual, auditory and olfactory input to the participant. The interface devices can also accept input from each participant for communication to the computing system. These inputs can be used for navigation and other manipulations of the virtual reality environment.

Each participant is associated with a given location or positional presence within the virtual reality environment. In one embodiment, this positional presence is expressed as 3D coordinates within the virtual reality environment. In one embodiment, the participant has a first-person view of the virtual reality environment with a point of view located at the positional presence of the participant. In another embodiment, the participant is provided with a third-party view of the virtual reality environment, and the positional presence of the participant is indicated, for example, by an avatar associated with the participant.

The computing system includes a product location module 110 that provides or associates a product location within the virtual reality environment with a product. In one embodiment, the product location module associates a plurality of products with a plurality of products locations within the virtual reality environment. Suitable products include, but are not limited to, any consumer product that can be ordered and delivered to a participant. The products include, but are not limited to, food, beverages, perfumes and flowers. In one embodiment, each product has one or more associated aromas, odors or smells that are unique or proprietary to that product. In one embodiment, each product has one or more unique or proprietary aromas, odors or smells associated with the physical location in which the product is displayed and sold. A proprietary aroma is an aroma that is unique to a product sold by a given proprietor and triggers an association between the aroma and the associated product in the mind of the participant receiving the aroma. A proprietor includes, but is not limited to, a manufacturer, wholesale distributor, retail distributor or advertiser of the product.

In one embodiment, each product location is a unique set of 3D coordinates within the virtual reality environment. In addition, the product locations are displayed or represented within the virtual reality environment, for example, as a virtual representation of a retail store, a restaurant, a counter, a table, a buffet, a cabinet, a refrigerator, a freezer, a bar, a warehouse or a service station. Each product location virtual representation can include branding associated with the product or the proprietor of the product in addition to virtual representations of the product. In one embodiment, a given product location is assigned by the product location module in accordance with an appropriate location within the virtual reality environment, e.g., within the context of the virtual reality environment. Alternatively, proprietors 112 that are in communication with the product location module select the product location for one or more of their products. In one embodiment, proprietors pay for or bid for one or more particular product locations within the virtual reality environment.

The computing system includes an aroma determination mechanism that is executing on the computing system to determine aromas associated with products. In one embodiment, the aroma determination mechanism identifies generic aromas associated with products based on the name or type of object. In another embodiment, the aroma determination mechanism identifies unique or proprietary aromas associated with products. In one embodiment, the unique or proprietary aromas are communicated to the aroma determination mechanism by one more proprietors of the products. Therefore, the aroma determination mechanism can identify and associate aromas with products. In one embodiment, the aromas are formulations of one more chemicals that are combined to achieve the desired aroma.

A spatial determination mechanism 116 executes on the computing system. The spatial determination mechanism monitors or obtains the coordinates of product locations and the positional presence of participants within the virtual reality environment. The spatial determination mechanism uses these coordinates to determine a distance and a direction from any given product location to any given positional presence of the participant. In addition, distances and directions are determined between product locations and between positional presences, i.e., between participants.

The system includes an aroma delivery mechanism 118 associated with each participant. Each aroma delivery mechanism is in close proximity to a given participant for delivering the desired or identified aroma or aromas to the associated participant. In one embodiment, the aroma delivery mechanism is close enough to a participant and configured to deliver a separate and unique aroma or intensity of aroma to each nostril of the participant. In one embodiment, each aroma delivery mechanism is associated with an interface device. For example, the aroma delivery mechanism is integrated into a HMD worn by the participant. In addition, the aroma delivery mechanism is in communication with the aroma determination mechanism and the spatial determination mechanism to deliver one or more product aromas to the participant in accordance with the distance and the direction between a product and a participant. In one embodiment, each aroma delivery mechanism stores or has access to chemicals or aromas that are combined in accordance with a formula communicated by the aroma determination mechanism to create the desired product aromas or aromas. Alternatively, the aroma delivery mechanism stores or has access to complete product aromas, for example, proprietary aromas provided by the proprietors of the products, and delivers a given aroma upon indication by the aroma determination mechanism.

As the positional presence of a participant changes or moves within the virtual reality environment, the distance and direction to a given product also changes. The spatial determination mechanism monitors these changes and works with the aroma determination mechanism to update the aromas delivered to a participant. These updates, i.e., changes in the overall intensity based on distance and changes in the intensity to a given nostril of the participant, are used to lead or to guide the participant through the virtual reality environment to the product location.

In general, generation, control and delivery of the aromas using the aroma delivery mechanism including variations in intensity involve using signals communicated from the computing system to the aroma delivery mechanism based on the determinations of the aroma determination mechanism and the spatial determination mechanism. This includes identifying the type and amount, i.e., concentration and flow rate, of various fragrances stored in the aroma determination mechanism or that can be obtained by the aroma determination mechanism. In addition, proprietary fragrances or aromas, i.e., complete fragrances, can also be identified.

For example, smell or aroma intensity determination and communication for an HMD is determined by the computing system operating the virtual reality environment, e.g., the game algorithm. The correct intensity or aroma delivered to each nostril is determined based on the distance and direction within in the virtual reality environment. A certain aroma compound, e.g., Benzyl Acetate which produces a fruity strawberry or pear smell, has a given odor detection threshold, e.g., 22 ppm. In general, aroma compounds typically have a molecular weight of less than approximately 300. The concentration of the aroma compound is delivered by the HMD is increased in proportion to the distance from the product location to the participant in the virtual reality environment. Products having aromas with lower odor detection thresholds are detectable across greater distances. The aroma delivery mechanism, i.e., HMD, regulates the concentration of the aroma compounds by changing the physical pathway and delivery from the cartridge or cartridges containing the aroma compounds to each nostril. Changing the physical pathway and delivery includes, but is not limited to, changing an aperture, using valves and controlling a flow rate of an air pump. In one embodiment, a maximum aroma output is calculated using the traits of a product to prevent participants from feeling ill, i.e., providing concentrations of aromas such as a hamburger smell that are beyond naturally occurring smells.

Therefore, the product aroma is delivered by varying at one of an intensity of the product aroma delivered to the participant based on the distance by comparing the distance a maximum distance within the virtual reality environment achievable by a threshold aroma intensity detection level associated with the product aroma and the intensity of the product aroma delivered to the participant separately to each nostril of the participant based on differences in the distance created by the direction. If the distance is greater than the maximum distance, then the level of aroma is below the threshold and no aroma is delivered. If the distance with equal to the maximum distance, then the threshold aroma intensity detection level is delivered. If the distance is less than the maximum, then an intensity of product aroma is delivered that increases above the threshold aroma intensity detection level as the distance decreases, for example, in proportion to the decrease in distance, subject to an upper intensity threshold. i.e., maximum aroma output.

A product acquisition module 120 executes on the computing system. The product acquisition module displays an interface within the virtual reality environment that can be used or manipulated by the participant to obtain actual physical copies or versions of the product or products outside of the virtual reality environment. The participant obtains the physical copies by ordering, purchasing or otherwise requesting the actual physical products from the product acquisition module using the displayed interface. The product acquisition module is in communication with the appropriate proprietor to communicate the request to obtain the product. In one embodiment, the product acquisition module accepts payment and verifies payment to the proprietors. In one embodiment, the product acquisition module running on the computing system controlling the virtual reality environment produces and displays the interface. Therefore, the computing system displays and controls the interface in the virtual reality environment. Alternatively, the interface is generated and displayed by a third party such as the proprietor of the product. The product acquisition module provides, for example, a shell within the virtual reality environment that a separate computing system associated with the third party or proprietor can use to display the interface. Interaction with the interface by the participant involves interacting directly with the separate computing system associated with the third party or proprietor.

The product acquisition module processes the request so that the desired product or products are delivered to the requesting participant. Suitable methods for delivery of the actual physical product include messenger services, drones, couriers, delivery drivers and shipping carriers. In one embodiment, the system also includes one or more databases 122 contained within the computing system or in communication with the computing system. The databases contain or store software required for execution of the modules and mechanisms of the computing systems, communications, order processing and payment processing, positional presences, products, product locations, aroma formulations and order histories.

Figure 2:
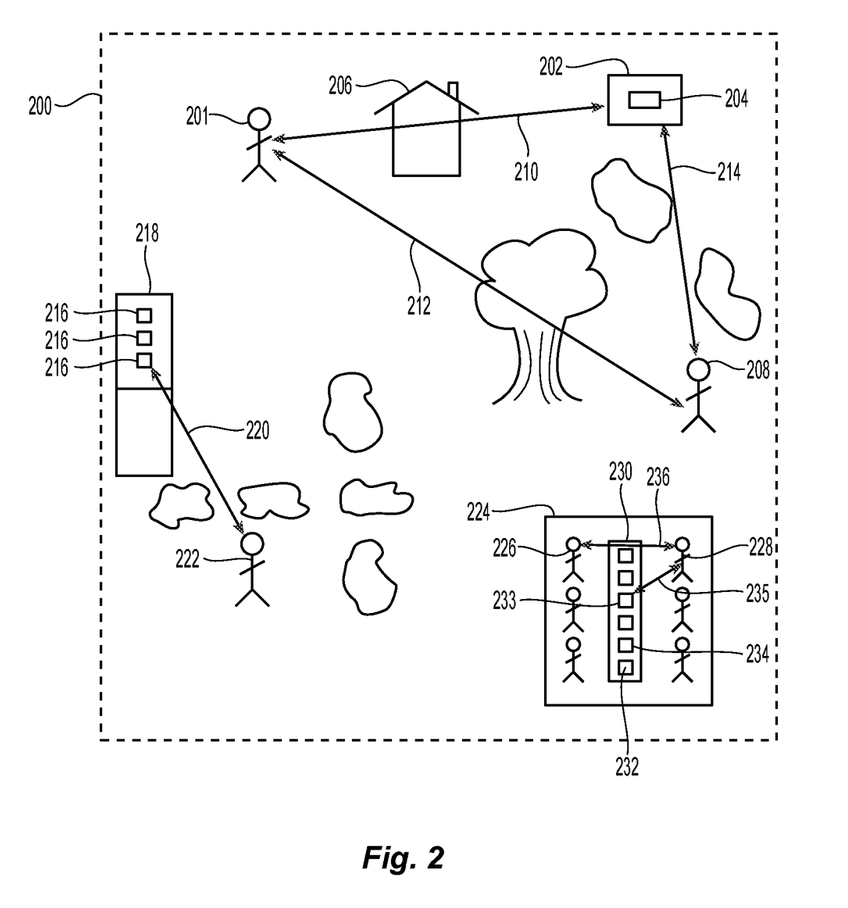
FIG. 2 is a schematic representation of an embodiment of a virtual reality environment.

Referring to FIG. 2, a representation of an embodiment of a virtual reality environment 200 is illustrated. An avatar 201 associated with a first participant is located within the virtual reality environment at a given set of 3D coordinates, i.e., (x,y,z), within the virtual reality environment. The 3D coordinates correspond to the positional presence or the participant or avatar. A product 204 is located at a given product location, e.g., a food kiosk or restaurant, having another set of 3D coordinates. The product location may not be directly viewable to the participant, especially in a first-person environment, due to intervening structures 206, topography or distance between the participant and product location. The coordinates of the participant or avatar and of the product location are used to determine the distance and direction 210 between the participant and product location for purposes of aroma delivery and using the aroma delivery to guide the participant to the product location, where the participant can acquire the product.

The virtual reality environment can also include one or more additional participants 208 or the avatars associated with those additional participants. Each additional participant is located at an additional positional presence having a unique set of 3D coordinates with the virtual reality environment. Aromas can also be communicated simultaneously to each additional participant. Communication of these aromas can be triggered by proximity of the additional participants to the first participant or to a given product location. For example, the aroma of the product 204 can be delivered to the additional participant upon at least one of obtaining a physical copy of the product by the first participant, delivery of the physical copy of the product to the first participant and use or consumption of the physical copy of the product by the first participant. In one embodiment, the product aroma is delivered to each additional participant based on an additional distance and an additional direction 214 from the product location to the additional positional presence of the additional participant within the virtual reality environment. In another embodiment, the product aroma is delivered to each additional participant based on an additional distance and an additional direction 212 from the positional presence of the first participant to the additional positional presence of the additional participant within the virtual reality environment.

In addition to communicating a single aroma associated with a single product at a single product location, multiple aromas are communication to the participant from multiple products located at multiple product locations. In one embodiment, these aromas are blended based upon the distance and direction to each product location. In one embodiment, a plurality of products 216 are located at a single product location 218. A given participant or avatar associated with the given participant 222 is located a given distance and direction 220 from the single product location. The aromas of the plurality of products are blended and delivered to the given participant and are used to direct the given participant to the single product location. Once at the single product location, the given participant is provided with the interface to obtain actual physical copies of one or more of the products associated with the product location. In one embodiment, a single product aroma from the plurality of products is communicated to the given participant. The single product aroma is selected based on a strong association between that product, the product location, i.e., a given restaurant, and all of the other products available at that product location. An example of a single product aroma includes, for example, french fries. In one embodiment, an aroma associated with the product location is communicated to the given participant, for example, the spices from an Italian deli, the smoke aroma from a grill or the popcorn from a movie rental site.

In one embodiment, a plurality of participants or the avatars associated with a plurality of participants are all located at a single general location 224 within the virtual reality environment. Suitable general locations include, for example, a sporting event, concert venue, college course, meeting or speech provided in a virtual reality environment and attended simultaneously by a plurality of participants. At least one product location 230 is provided in the single general location. The product location can be, for example, a buffet or a table containing a plurality of products 234, for example, food and beverages, available for order or purchase and delivery to the actual participants. A first participant 226 is provided with the aromas from the plurality of products and decides to order a first product 233 from the single product location. The first product is delivered to the first participant. While the first participant is enjoying the first product, the aroma associated with the first product is delivered to a second participant 228 based on either the distance and direction 235 between the second participant and the first product or the distance and direction 236 between the second participant and the first participant. Therefore, the second participant knows that the first participant has ordered a given product and may use this information in determining to acquire or purchase the same product.

Figure 3:
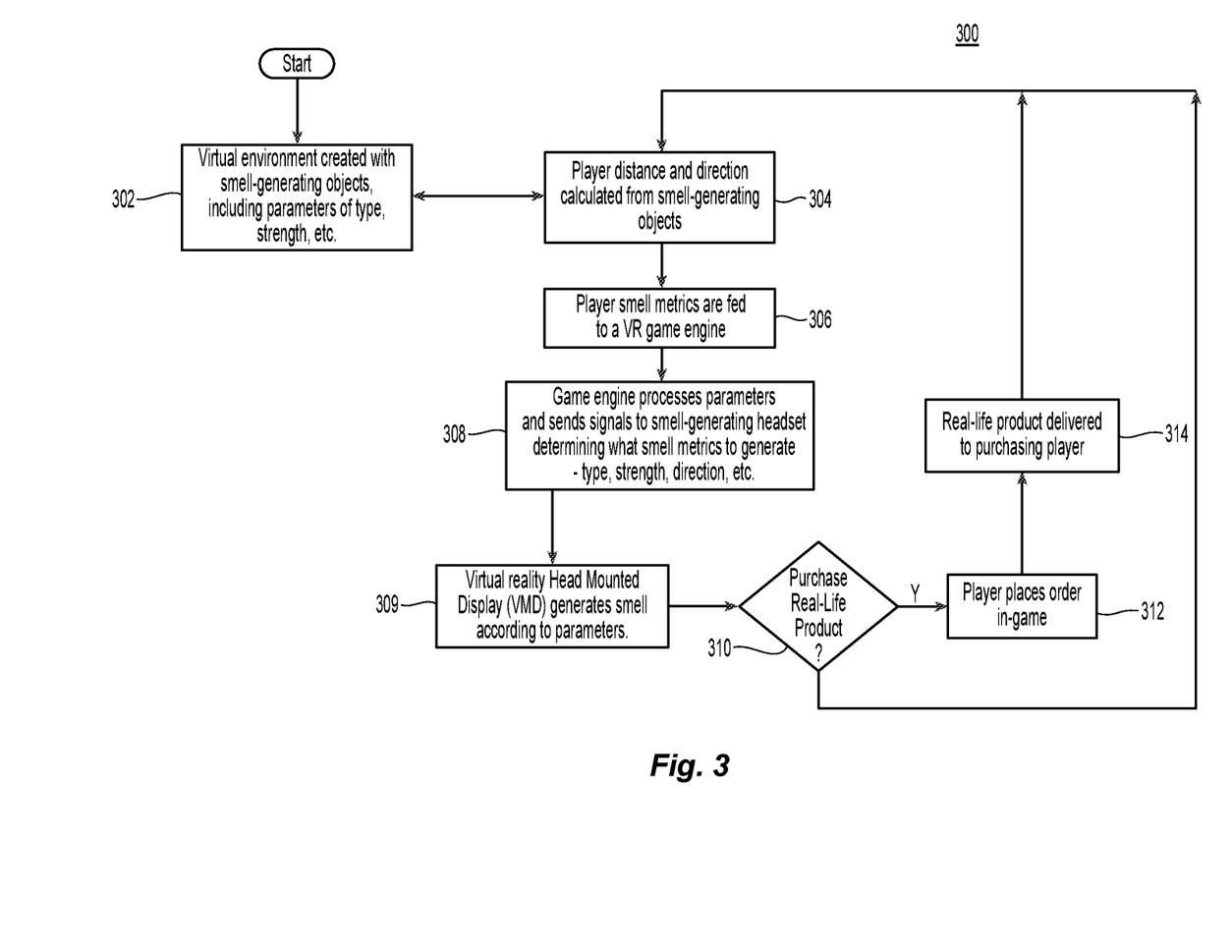
FIG. 3 is a flow chart illustrating an embodiment of a method for using three-dimensional positional spatial olfaction for virtual marketing.

Referring now to FIG. 3, an exemplary embodiment for marketing products to players in a virtual gaming environment 300 is illustrated. A virtual reality environment that is a virtual gaming environment is created 302 containing one or more participants or players and a plurality of aroma or smell generating object or products. Creation of the aroma generating products takes into account the type of aroma, the strength of the aroma and the location of the product within the gaming environment. For each player, a distance and a direction are calculated from the aroma generating objects 304. The metrics, i.e., distance and direction, for each player are communicated to the computing system running the gaming environment, e.g., the virtual reality game engine 306. The distance and direction in combination with the type and strength of the aromas for the products are used to send appropriate instructions or signals to the headsets or head-mounted displays associated with each player 308. These signals and instructions are used by the aroma or smell generating HMDs to generate the appropriate aromas or smells for each player 309. Each player, upon receiving the generated aromas, determines whether to purchase an actual, physical, real-life product 310. If a player decides to purchase a real-life product, the player uses the spatial queues of direction and distance provided with the aromas to find the location of the interface within the gaming environment for the product associated with the aroma and to use the interface to place an order for that product 312. The real-life product is then delivered to the player 314, for example, using a package carrier or a drone. Following delivery, or if the player decides not to purchase a product, the monitoring of player location and communication of aromas continues.

Figure 4:
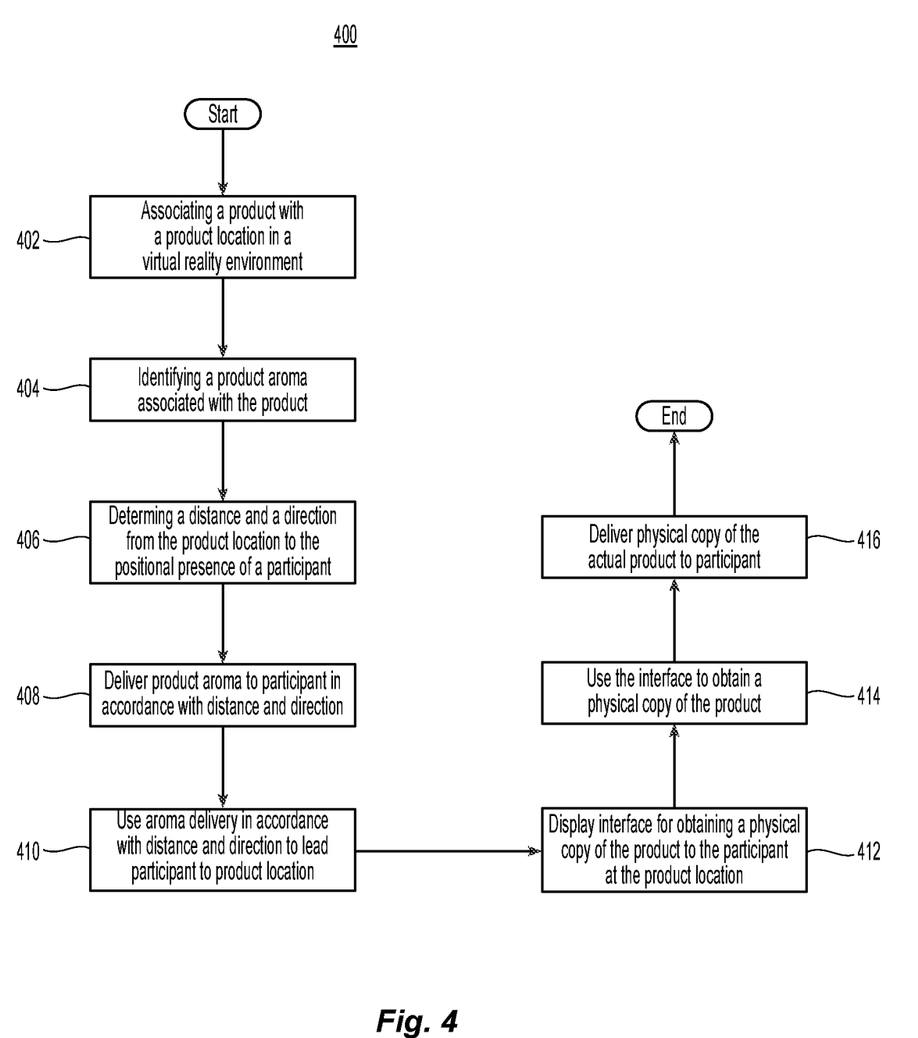
FIG. 4 is a flow chart illustrating another embodiment of a method for using three-dimensional positional spatial olfaction for virtual marketing.

Referring now to FIG. 4, another exemplary embodiment of a method for using three-dimensional positional spatial olfaction for virtual marketing 400 is illustrated. A product is associated with a product location within a virtual reality environment 402. Suitable products include, but are not limited to, a food and a beverage. In one embodiment, the product location is a three-dimensional coordinate in the virtual reality environment. Suitable product locations can be displayed as a virtual representation of a retail store, a restaurant, a counter, a table, a buffet, a cabinet, a refrigerator, a freezer, a bar, a warehouse or a service station. In one embodiment, a proprietor of the product is allowed to or provided with the opportunity to select a product location within the virtual reality environment, for example, through purchasing that product location.

A product aroma associated with the product is identified 404. In one embodiment, at least one of an aroma emanating from the product, an aroma associated with the product location containing the product and a proprietary aroma associated with the product is used to identify the associated aroma. In one embodiment, the associated aroma is a generic aroma. In another embodiment, the associated aroma is a propriety aroma provided by the proprietor of the product. A distance and a direction from the product location to a positional presence of a participant within the virtual reality environment is determined 406. In one embodiment, the positional presence is a three-dimensional coordinate within the virtual reality environment.

The product aroma is delivered to the participant in accordance with the distance and the direction 408. In one embodiment, a head-mounted display worn by the participant is used to deliver the product aroma. The head-mounted display includes an integrated aroma generator or dispenser that can varying the type and intensity of the aroma individually to each nostril of the participant. In one embodiment, at least one of an intensity of the product aroma delivered to the participant based on the distance and an intensity of the product aroma delivered separately to each nostril of the participant based on the direction is varied. This communicates both distance and directional information to the participant. Therefore, delivery of the product aroma to the participant in accordance with the distance and the direction is used to lead the participant through the virtual reality environment to the product location 410. In one embodiment, at least one of an overall intensity of the product aroma delivered to the participant and each separate intensity of the product aroma delivered to each nostril of the participant are modified in response to changes in the distance and the direction between the product location and the participant to lead the participant to the product location within the virtual reality environment.

An interface for obtaining a physical copy of the product is displayed to the participant within the virtual reality environment at the product location 412. The physical copy of the product is the actual physical product. The participant uses the interface within the virtual reality environment to obtain at least one physical copy of the product 414. In one embodiment, the participant purchases the product. The physical copy of the product is delivered to the participant 416. Any suitable method for delivering products to purchasers can be used, including drones, couriers and package delivery companies. In one embodiment, the actual physical product is delivered to the participant, and used or consumed by the participant, during or concurrent with the active presence of the participant within the virtual reality environment. Therefore, the active use or consumption of the product, e.g., a meal or beverage, is communicated to other active participants in the virtual reality environment.

In one embodiment, the product aroma is delivered to at least one additional participant at an additional positional presence within the virtual reality environment associated with the additional participant. Delivery of the product aroma to additional participants can be triggered upon at least one of obtaining, ordering or purchasing a physical copy of the product by the participant, delivery of the physical copy of the product to the participant and use of the physical copy of the product by the participant, in particular during the virtual reality environment session.

In one embodiment, the product aroma is delivered to the at least one additional participant based on an additional distance and an additional direction from the product location to the additional positional presence of the additional participant within the virtual reality environment. Alternatively, the product aroma is delivered to the at least one additional participant based on an additional distance and an additional direction from the positional presence of the participant to the additional positional presence of the additional participant within the virtual reality environment, i.e., the relative positions between participants.

Figure 5:
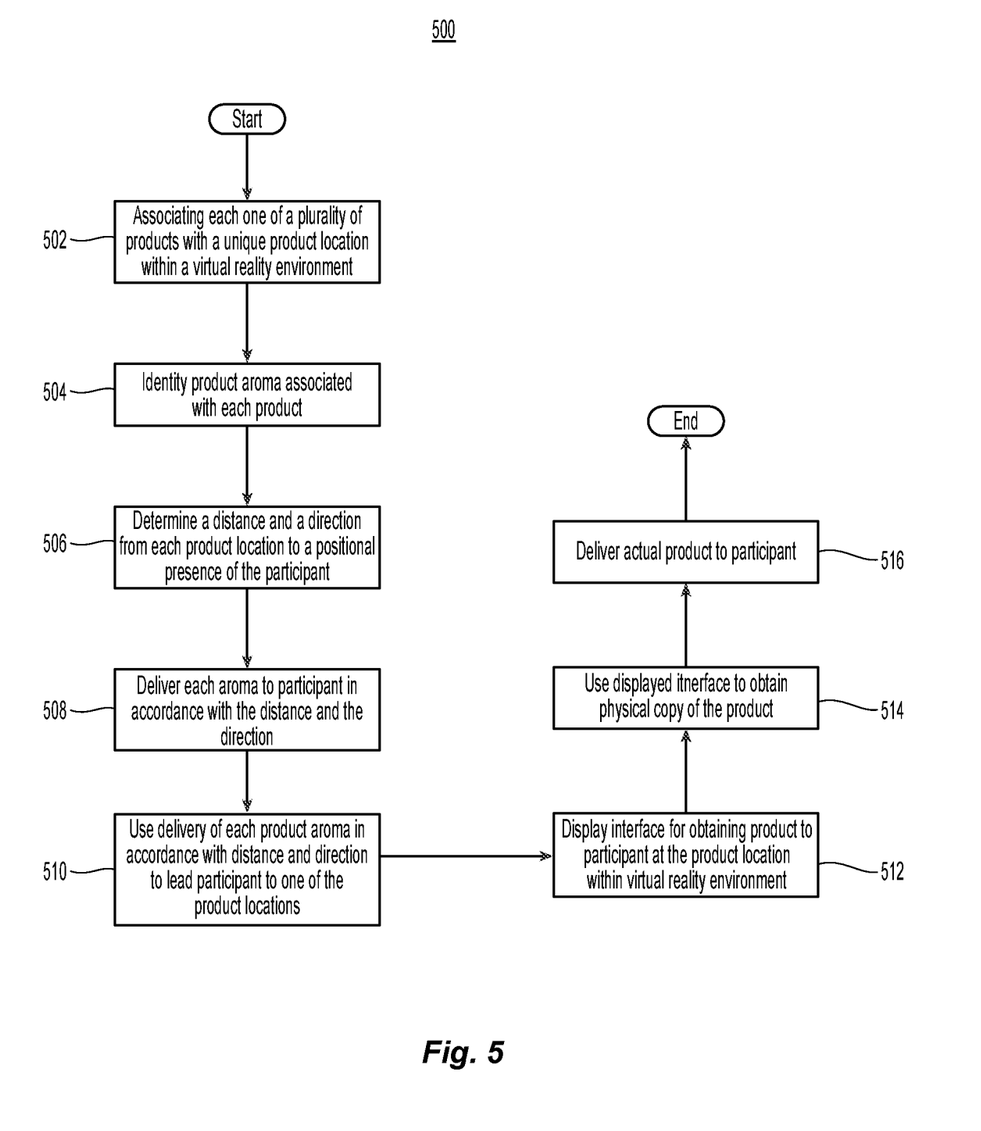
FIG. 5 is a flow chart illustrating yet another embodiment of a method for using three-dimensional positional spatial olfaction for virtual marketing.

Referring now to FIG. 5, another embodiment of a method for using three-dimensional positional spatial olfaction for virtual marketing 500 is illustrated. This embodiment is directed to the delivery of multiple aromas from multiple products at multiple products locations to at least one or multiple participants within a given virtual reality environment. All features discussed with respect to embodiments of other systems and methods can be used with this embodiment. Each one of a plurality of products is associated with a unique product location within a virtual reality environment 502. A product aroma associated with each product is identified 504. A distance and a direction from each product location to a positional presence of a participant within the virtual reality environment are determined 506. In one embodiment, a distance and a direction are determined from each product location to a plurality of positional presences associated with a plurality of participants within the virtual reality environment.

Each product aroma is delivered to the participant in accordance with the distance and the direction 508. In one embodiment, at least one of an intensity of each product aroma delivered to the participant based on the distance to each product location and an intensity of each product aroma delivered to the participant separately to each nostril of the participant based on the direction to each product location is varied to produce a blended aroma that is delivered to the participant. In one embodiment, each product aroma is delivered to each one of the plurality of participants in accordance with the distance and the direction associated with each participant. The delivery of each product aroma to the participant in accordance with the distance and the direction is used to lead the participant through the virtual reality environment to at least one of the product locations 510. In one embodiment, the delivery of each product aroma to each one of a plurality of participants in accordance with the distance and the direction is used to lead one or more participants through the virtual reality environment to at least one of the product locations.

An interface for obtaining a physical copy of a given product is displayed to the participant within the virtual reality environment at the product location associated with the given product 512. In one embodiment, an interface for obtaining a physical copy of a given product is displayed to one or more participants within the virtual reality environment at the product location associated with the given product. The participant uses the interface to obtain at least one physical copy of the given product 514, and the physical copy of the given product to the participant 516.

Exemplary embodiments enhance the effectiveness of product placement in virtual environments using, for example, virtual reality headsets with integrated smell or aroma generators into the HMDs. Base smells are combined into appealing smells ranging, for example, from cinnamon buns to french fries. These aroma-enabled headsets deliver aromas to each nostril with varying intensity, which allows users to localize and to track the aromas in 3D space. As a participant wearing the HMD turns their head towards the product location of the product generating the aroma, both nostrils receive equal amounts of the aroma, informing the participant that the product or object is located in front of them. As the participant or the avatar associated with the participant approaches the product location, the aroma intensity increases, informing the participant that they are approaching the location of the product.

Exemplary embodiments, therefore, use olfaction within a virtual reality environment to advertise products. This olfactory advertising is more interactive and engaging than conventional commercials, less obtrusive, and allows multiple proprietors, e.g., a plurality of food vendors to compete concurrently and simultaneously in a single common virtual reality environment, i.e., the virtual world. In one embodiment, proprietors, e.g., business marketers, send proprietary smell capsules with virtual reality (VR) program distribution.

In one exemplary application in accordance with exemplary embodiments, a new virtual reality videogame is released, and product proprietors or marketers bid for olfactory advertising space in the virtual world. A first participant, while exploring the virtual reality environment, begins to smell french fries. Even if the first participant was not initially hungry or looking for food, the first participant follows the aromas and discovers a virtual representation of a restaurant, for example a branded storefront of a fast-food restaurant, displayed in the virtual reality videogame environment. The first participant approaches the virtual representation and places an order, for french fries or any other product on a displayed menu, via an in-game menu screen. A real-life order is generated, and is delivered, for example via conventional delivery or drone drop. When the first participant's real-life order has arrived, an in-game notification is provided to the first participant to alert the first participant.

In another exemplary application, a first participant is viewing a sporting event using Social VR. A plurality of additional participants are also watching the sporting even using Social VR; however, the actual physical locations of the participants are dispersed over a large geographical area. Each participant wears a VR headset and find themselves sharing a virtual couch located in a virtual living room. The participants can talk with each other and watch the game together. The virtual living room contains a buffet table on which representations of food and beverages available, for example, from major retailers are displayed. The first participant receives a faint aroma from one of the displayed products, e.g., spicy chicken wings, while seated on the coach. The first participant stands and approaches the virtual buffet table. As the first participant gets closer to the table, the aroma intensity increases. The first participant can smell individual aromas distinctly while moving from one food item to the other, and the aroma intensity increases as the first participant leans in for a better look at a particular product, e.g., nachos with cheese. The first participant orders one or more of the products using a pop-up virtual menu, and the food is delivered to the physical address of the first participant. The first participant begins consuming the delivered products, and the aromas associated with those products are projected through the Social VR to the additional participants. This encourages additional participants to also purchase those products.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

It is to be understood that although a detailed description on cloud computing is provided, implementation of the teachings provided herein are not limited to a cloud computing environment. Rather, embodiments of the present invention are capable of being implemented in conjunction with any other type of computing environment now known or later developed. Cloud computing is a model of service delivery for enabling convenient, on-demand network access to a shared pool of configurable computing resources, e.g., networks, network bandwidth, servers, processing, memory, storage, applications, virtual machines, and services, that can be rapidly provisioned and released with minimal management effort or interaction with a provider of the service.

This cloud model may include at least five characteristics, at least three service models, and at least four deployment models. The five characteristics are on-demand self-service, broad network access, resource pooling, rapid elasticity and measured service. Regarding on-demand self-service, a cloud consumer can unilaterally provision computing capabilities, such as server time and network storage, as needed automatically without requiring human interaction with the service's provider. Broad network access refers to capabilities that are available over a network and accessed through standard mechanisms that promote use by heterogeneous thin or thick client platforms, e.g., mobile phones, laptops, and PDAs. For resource pooling, the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction, e.g., country, state, or datacenter. Rapid elasticity refers to capabilities that can be rapidly and elastically provisioned, in some cases automatically, to quickly scale out and rapidly released to quickly scale in. To the consumer, the capabilities available for provisioning often appear to be unlimited and can be purchased in any quantity at any time. For measured service, cloud systems automatically control and optimize resource use by leveraging a metering capability at some level of abstraction appropriate to the type of service, e.g., storage, processing, bandwidth, and active user accounts. Resource usage can be monitored, controlled, and reported, providing transparency for both the provider and consumer of the utilized service.

The three service models are Software as a Service (SaaS), Platform as a Service (PaaS) and Infrastructure as a Service (IaaS). Software as a service provides the capability to the consumer to use the provider's applications running on a cloud infrastructure. The applications are accessible from various client devices through a thin client interface such as a web browser, e.g., web-based e-mail. The consumer does not manage or control the underlying cloud infrastructure including network, servers, operating systems, storage, or even individual application capabilities, apart from limited user-specific application configuration settings. Platform as a service provides the capability to the consumer to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations. Infrastructure as a service provides the capability to the consumer to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components, e.g., host firewalls.

The Deployment Models are private cloud, community cloud, public cloud and hybrid cloud. The private cloud infrastructure is operated solely for an organization. It may be managed by the organization or a third party and may exist on-premises or off-premises. The community cloud infrastructure is shared by several organizations and supports a specific community that has shared concerns, e.g., mission, security requirements, policy, and compliance considerations. It may be managed by the organizations or a third party and may exist on-premises or off-premises. The public cloud infrastructure is made available to the general public or a large industry group and is owned by an organization selling cloud services. The hybrid cloud infrastructure is a composition of two or more clouds (private, community, or public) that remain unique entities but are bound together by standardized or proprietary technology that enables data and application portability, e.g., cloud bursting for load-balancing between clouds.

Figure 6:
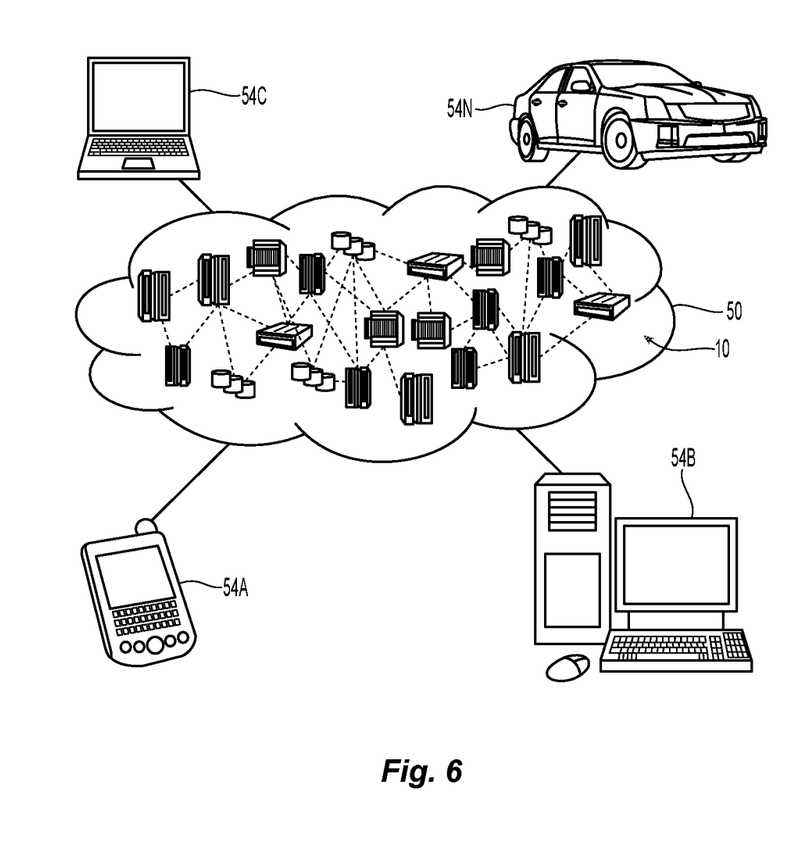
FIG. 6 depicts a cloud computing environment according to an embodiment of the present invention.

A cloud computing environment is service oriented with a focus on statelessness, low coupling, modularity, and semantic interoperability. At the heart of cloud computing is an infrastructure that includes a network of interconnected nodes. Referring now to FIG. 6, an illustrative cloud computing environment 50 is depicted. As shown, the cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 6 are intended to be illustrative only and that computing nodes 10 and cloud computing environment 50 can communicate with any type of computerized device over any type of network and/or network addressable connection, e.g., using a web browser.

Figure 7:
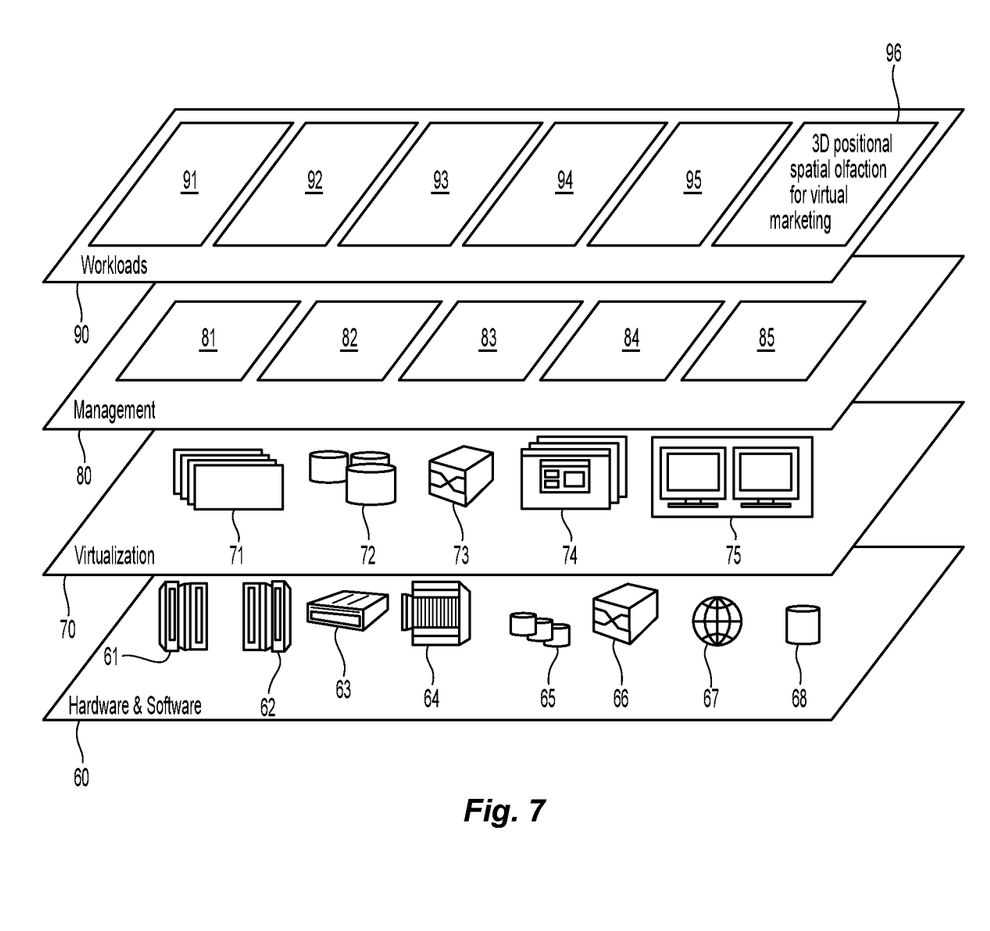
FIG. 7 depicts abstraction model layers according to an embodiment of the present invention.

Referring now to FIG. 7, a set of functional abstraction layers provided by cloud computing environment 50 (FIG. 6) is shown. It should be understood in advance that the components, layers, and functions shown in FIG. 7 are intended to be illustrative only and embodiments of the invention are not limited thereto. As depicted, the following layers and corresponding functions are provided. A hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68. A virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and using three-dimensional positional spatial olfaction for virtual marketing 96.

Methods and systems in accordance with exemplary embodiments of the present invention can take the form of an entirely hardware embodiment, an entirely software embodiment or an embodiment containing both hardware and software elements. In a preferred embodiment, the invention is implemented in software, which includes but is not limited to firmware, resident software and microcode. In addition, exemplary methods and systems can take the form of a computer program product accessible from a computer-usable or computer-readable medium providing program code for use by or in connection with a computer, logical processing unit or any instruction execution system. For the purposes of this description, a computer-usable or computer-readable medium can be any apparatus that can contain, store, communicate, propagate, or transport the program for use by or in connection with the instruction execution system, apparatus, or device. Suitable computer-usable or computer readable mediums include, but are not limited to, electronic, magnetic, optical, electromagnetic, infrared, or semiconductor systems (or apparatuses or devices) or propagation mediums. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-RAY) and DVD.

Suitable data processing systems for storing and/or executing program code include, but are not limited to, at least one processor coupled directly or indirectly to memory elements through a system bus. The memory elements include local memory employed during actual execution of the program code, bulk storage, and cache memories, which provide temporary storage of at least some program code in order to reduce the number of times code must be retrieved from bulk storage during execution. Input/output or I/O devices, including but not limited to keyboards, displays and pointing devices, can be coupled to the system either directly or through intervening I/O controllers. Exemplary embodiments of the methods and systems in accordance with the present invention also include network adapters coupled to the system to enable the data processing system to become coupled to other data processing systems or remote printers or storage devices through intervening private or public networks. Suitable currently available types of network adapters include, but are not limited to, modems, cable modems, DSL modems, Ethernet cards and combinations thereof.

In one embodiment, the present invention is directed to a machine-readable or computer-readable medium containing a machine-executable or computer-executable code that when read by a machine or computer causes the machine or computer to perform a method for using three-dimensional positional spatial olfaction for virtual marketing in accordance with exemplary embodiments of the present invention and to the computer-executable code itself. The machine-readable or computer-readable code can be any type of code or language capable of being read and executed by the machine or computer and can be expressed in any suitable language or syntax known and available in the art including machine languages, assembler languages, higher level languages, object oriented languages and scripting languages. The computer-executable code can be stored on any suitable storage medium or database, including databases disposed within, in communication with and accessible by computer networks utilized by systems in accordance with the present invention and can be executed on any suitable hardware platform as are known and available in the art including the control systems used to control the presentations of the present invention.

While it is apparent that the illustrative embodiments of the invention disclosed herein fulfill the objectives of the present invention, it is appreciated that numerous modifications and other embodiments may be devised by those skilled in the art. Additionally, feature(s) and/or element(s) from any embodiment may be used singly or in combination with other embodiment(s) and steps or elements from methods in accordance with the present invention can be executed or performed in any suitable order. Therefore, it will be understood that the appended claims are intended to cover all such modifications and embodiments, which would come within the spirit and scope of the present invention.

What is claimed is:

1. A method for using three-dimensional positional spatial olfaction for virtual marketing, the method comprising:
   determining a distance and a direction from a product location within a virtual reality environment associated with a product to a positional presence of a participant within the virtual reality environment;
   delivering a product aroma associated with the product to the participant in accordance with the distance and the direction;
   communicating, by an aroma delivery mechanism, distance and directional information of the product location in the virtual reality environment by delivering the product aroma to the participant;
   wherein delivering the product aroma comprises at least one of varying an intensity of the product aroma delivered to the participant based on the distance by comparing the distance to a maximum distance within the virtual reality environment achievable by a threshold aroma intensity detection level associated with the product aroma and varying intensity of the product aroma delivered to the participant separately to each nostril of the participant based on differences in the distance created by the direction; and
   wherein the method further comprises using the interface to obtain at least one physical copy of the product.

2. The method of claim 1, wherein the method further comprises displaying an interface for obtaining a physical copy of the product to the participant within the virtual reality environment at the product location.

3. The method of claim 1, wherein the product location and the positional presence comprise three-dimensional coordinates in the virtual reality environment.

4. The method of claim 1, wherein the product location comprises a virtual representation of a retail store, a restaurant, a counter, a table, a buffet, a cabinet, a refrigerator, a freezer, a bar, a warehouse or a service station.

5. The method of claim 1, wherein the method further comprises identifying the product aroma using at least one of an aroma emanating from the product, an aroma associated with the product location containing the product and a proprietary aroma associated with the product to identify the product aromas.

6. The method of claim 1, wherein delivering the product aroma comprises using a head-mounted display worn by the participant to deliver the product aroma.

7. The method of claim 1, wherein using delivery of the product aroma comprises modifying at least one of an overall intensity of the product aroma delivered to the participant and each separate intensity of the product aroma delivered to each nostril of the participant in response to changes in the distance and the direction.

8. The method of claim 1, wherein the method further comprises delivering the physical copy of the product to the participant.

9. The method of claim 1, wherein the method further comprises delivering the product aroma to at least one additional participant at an additional positional presence within the virtual reality environment associated with the additional participant upon at least one of obtaining a physical copy of the product by the participant, delivery of the physical copy of the product to the participant and use of the physical copy of the product by the participant.

10. The method of claim 9, wherein delivering the product aroma to the at least one additional participant comprises delivering the product aroma to the at least one additional participant based on an additional distance and an additional direction from the product location to the additional positional presence of the additional participant within the virtual reality environment.

11. The method of claim 9, wherein delivering the product aroma to the at least one additional participant comprises delivering the product aroma to the at least one additional participant based on an additional distance and an additional direction from the positional presence of the participant to the additional positional presence of the additional participant within the virtual reality environment.

12. The method of claim 1, wherein the method further comprises allowing a proprietor of the product to select the product location within the virtual reality environment.

13. A method for using three-dimensional positional spatial olfaction for virtual marketing, the method comprising:
determining a distance and a direction from each one of a plurality of unique product locations to a positional presence of a participant within the virtual reality environment, each unique product location associated with one of a plurality of products;
delivering each one of a plurality of product aromas associated with one of the products to the participant in accordance with the distance and the direction;
communicating, by an aroma delivery mechanism, distance and directional information of the product location in the virtual reality environment by delivering the product aroma to the participant;
wherein delivering the product aroma comprises at least one of varying an intensity of the product aroma delivered to the participant based on the distance by comparing the distance to a maximum distance within the virtual reality environment achievable by a threshold aroma intensity detection level associated with the product aroma and varying intensity of the product aroma delivered to the participant separately to each nostril of the participant based on differences in the distance created by the direction; and
wherein the method further comprises using the interface to obtain at least one physical copy of the product.

14. The method of claim 13, wherein:
determining a distance and a direction comprises determining a distance and a direction from each product location to a plurality of positional presences associated with a plurality of participants within the virtual reality environment;
delivering each product aroma comprises delivering each product aroma to each one of the plurality of participants in accordance with the distance and the direction associated with each participant; and
using delivery of each product aroma comprises using delivery of each product aroma to each participant in accordance with the distance and the direction to lead one or more participants through the virtual reality environment to at least one of the product locations.

15. The method of claim 13, wherein the method further comprises:
displaying an interface for obtaining a physical copy of a given product to the participant within the virtual reality environment at the product location associated with the given product;
using the interface to obtain at least one physical copy of the given product; and
delivering the physical copy of the given product to the participant.

16. A system for using three-dimensional positional spatial olfaction for virtual marketing, the system comprising:
a computing system running an instance of a virtual reality environment;
an interface device in communication with the computing system and associated with a participant, the interface device providing display of the virtual reality environment to the participant at a positional presence within the virtual reality environment;
a product location module executing on the computing system to associate a product location within the virtual reality environment with a product;
an aroma determination mechanism executing on the computing system to determine an aroma associated with the product;
a spatial determination mechanism executing on the computing system to determining a distance and a direction from the product location to the positional presence of the participant;
an aroma delivery mechanism associated with the interface device and in communication with the aroma determination mechanism and the spatial determination mechanism to communicate distance and directional information of the product location in the virtual reality environment by delivering the product aroma to the participant;
wherein delivering the product aroma comprises at least one of varying an intensity of the product aroma delivered to the participant based on the distance by comparing the distance to a maximum distance within the virtual reality environment achievable by a threshold aroma intensity detection level associated with the product aroma and varying intensity of the product aroma delivered to the participant separately to each nostril of the participant based on differences in the distance created by the direction; and
a product acquisition module executing on the computing system to display an interface for obtaining a physical copy of the product to the participant within the virtual reality environment at the product location.

17. The system of claim 16, wherein the product acquisition module receives a request for at least one physical copy of the product through the interface and processes the request to deliver the physical copy of the given product to the participant.

* * * * *